United States Patent [19]

Chen et al.

[11] Patent Number: 5,045,206
[45] Date of Patent: Sep. 3, 1991

[54] SELECTIVE MULTI-RING AROMATICS EXTRACTION USING A POROUS, NON-SELECTIVE PARTITION MEMBRANE BARRIER

[75] Inventors: Tan-Jen Chen, Clearwater, Canada; James R. Sweet, Baton Rouge, La.

[73] Assignee: Exxon Research & Engineering Company, Florham Park, N.J.

[21] Appl. No.: 622,706

[22] Filed: Dec. 5, 1990

[51] Int. Cl.$^5$ .............................................. B01D 3/00
[52] U.S. Cl. .................................... 210/640; 210/644; 210/649; 210/655; 210/651; 55/16; 55/158; 585/819
[58] Field of Search ............... 210/649, 650, 651, 653, 210/654, 640, 500.23, 500.21, 490, 321.6, 500.36, 644; 55/16; 585/819; 208/321, 331; 502/4

[56] References Cited

U.S. PATENT DOCUMENTS

| | | | |
|---|---|---|---|
| 2,930,754 | 3/1960 | Stuckey | 210/23 |
| 2,947,687 | 8/1960 | Lee | 210/23 |
| 2,956,112 | 5/1976 | Lee et al. | 210/22 |
| 2,958,656 | 11/1960 | Stuckey | 210/23 |
| 3,043,891 | 7/1962 | Stuckey | 260/674 |
| 3,140,256 | 7/1964 | Martin et al. | 210/23 |
| 3,244,763 | 4/1966 | Cahn | 260/677 |
| 3,305,595 | 2/1967 | Paulson | 210/644 |
| 3,320,328 | 5/1967 | Michaels | 210/644 |
| 3,370,102 | 2/1968 | Carpenter et al. | 260/674 |
| 3,725,255 | 4/1973 | Barilli et al. | 208/331 |
| 3,725,256 | 4/1973 | Lugo | 208/331 |
| 3,725,257 | 4/1973 | Cavenaghi et al. | 208/331 |
| 4,115,465 | 9/1978 | Elfert et al. | 260/674 |
| 4,239,506 | 12/1980 | Steigelmann et al. | 210/651 |
| 4,510,047 | 4/1985 | Thompson | 210/655 |
| 4,510,097 | 4/1985 | Thompson | 208/321 |
| 4,532,347 | 7/1985 | Vaughan | 562/528 |
| 4,670,151 | 6/1987 | Bitter | 210/641 |
| 4,797,200 | 6/1989 | Osterhuber | 210/651 |
| 4,837,054 | 6/1989 | Schucker | 427/244 |
| 4,861,628 | 8/1989 | Schucker | 427/245 |
| 4,914,064 | 4/1990 | Schucker | 502/4 |
| 4,929,357 | 5/1990 | Schucker | 210/640 |
| 4,929,358 | 5/1990 | Koenitzer | 210/640 |
| 4,962,270 | 10/1990 | Feimer et al. | 210/640 |
| 4,962,271 | 10/1990 | Black et al. | 585/819 |
| 4,966,707 | 10/1990 | Cussler et al. | 210/632 |

FOREIGN PATENT DOCUMENTS 1000413  1/1986  Japan .................................... 210/649

OTHER PUBLICATIONS

"Microporous Membrane Solvent Extraction", Prasad, R. et al., Separation Science & Technology 22 (2&3) 619-640, 1987.
"Dispersion-Free Solvent Extraction with Microporous Hollow Fiber Modules", Prasad, R. et al., AIChE Summer National Meeting, Boston, 1986.
"Designing Hollow-Fiber Contactors", Yang, M. C. et al., AIChe Journal, Nov. 1986, vol. 32, No. 11, pp. 1910-1916.
"Liquid-Liquid Extractions with Microporous Hollow Fibers", D'Elia, N. A. et al., J. Memb. Sci. 29 (1986) 309-319.
"Critical Entry Pressure for Liquids in Hydrophobic Membranes", Kim. B. S. et al., J. Coll. & Interface Science, vol. 115, No. 1, 1987, pp. 1-8.
"Solvent Extraction with Microporous Hydrophilic and Composite Membranes", Prasad, R. et al., AIChE Journal, vol. 33, No. 7, (1987) pp. 1057-1066.
"Dispersion-Free Solvent Extraction with Microporous Hollow Fiber Modules" Prasad, R. et al., AIChE Journal, vol. 34, No. 2, (1988), pp. 177-187.
"Nondispersive Solvent Extraction Using Microporous Membranes", Prasad, R. et al., AIChE Symposium Series, Membrane Materials & Proc. No. 261, vol. 84, 1988, pp. 42-53.
"Hollow Fiber Solvent Extraction of Pharmaceutical Products: A Case Study", Prasad, R. et al., J. Memb. Sci. 47, (1989), 235-259.
"Novel Uses of Microporous Membranes, A Case Study", R. W. Callahan, AIChE Symposium Series, Membrane Materials and Process, No. 261, vol. 84, 1988, pp. 54-65.

Primary Examiner—Robert A. Dawson
Assistant Examiner—Ana Fortuna
Attorney, Agent, or Firm—Joseph J. Allocca

[57] ABSTRACT

Multi-ring aromatic hydrocarbons and/or toxins are selectively solvent extracted from hydocarbon feed streams by the process comprising contacting the aromatics and/or toxins containing hydrocarbon stream with one side of a porous, non-selective partition barrier membrane while simultaneously contacting the other side of said membrane with an aromatics selective extraction solvent whereby the multi-ring aromatic hydrocarbons and/or toxins selectively migrate through the porous partition barrier membrane in response to the selective solvent. A preferred extraction solvent is ethylenediamine. The permeate comprising multi-ring aromatics in solvent can be subjected to a membrane separation process to separate the extraction solvent from the aromatics.

5 Claims, No Drawings

SELECTIVE MULTI-RING AROMATICS EXTRACTION USING A POROUS, NON-SELECTIVE PARTITION MEMBRANE BARRIER

BRIEF DESCRIPTION OF THE INVENTION

Multi-ring-aromatic hydrocarbons and toxins present in various hydrocarbon streams such as fuels and lubricating oils, transformer oils, refrigerator oils, turbine oils, white oils etc., are selectively removed from said hydrocarbon streams by a process involving contacting the aromatics containing hydrocarbon feed stream with one side of a non-selective, porous, partition barrier membrane while simultaneously contacting the other side of the membrane with a selective aromatics extraction solvent such as phenol, furfural, sulfolane, acetonitrile, n-methyl pyrrolidone dimethylsulfoxide (DMSO) or, preferably, an aliphatic polyamine such as ethylene diamine, diethylene triamine or triethylene-tetramine. The porous partition barrier membrane, while not contributing to the selectivity of the separation process, does prevent or minimize the intermingling of the feed and the extraction solvent which is typical of conventional solvent extraction processes. The membrane permits the feed and extraction solvent to share a large contacting surface area while preventing the intermingling of the two phases. The multi-ring aromatic hydrocarbons and/or toxins in the feed selectively permeate through the porous barrier in response to the selective extraction solvent to produce a multi-ring aromatic and/or toxin rich permeate phase. This permeate phase containing multi-ring aromatic hydrocarbons and/or toxins and extraction solvent can itself be separated into its components by distillation, or, preferably, the energy efficient membrane separation processes now being described in the literature.

BACKGROUND OF THE INVENTION

Treatment of aromatics containing hydrocarbon feed streams to selectively remove the aromatics therefrom is a conventional hydrocarbon treatment process. The aromatics are typically removed by the use of solvents which are selective for the aromatic hydrocarbons. Solvents which have been used for that purpose have included phenol, furfural, sulfolane, and n-methyl pyrrolidone to name just a few of the better known or more widely used solvents.

The treatment process usually involves the counter-current contacting of the aromatics containing hydrocarbon stream with the selective extraction solvent in a tall, usually vertical multi trayed or packed treater tower. Massive quantities of hydrocarbon feed are intimately mixed with equally massive volumes of extraction solvent to produce multi phase emulsions which, at the extreme ends of the treater tower separate by gravity into an aromatics lean raffinate phase and an aromatics rich extract phase which also contains the bulk of the selective solvent.

Because the separation of the multi-component emulsion in the treater tower is effected by gravity, it is essential that the density differences between the hydrocarbon feed and the extraction solvent be sufficiently great so that the separation can be accomplished in a reasonable length of time. Because of this restriction and also because of the tremendous volumes of material handled, it would be desirable if aromatics could be removed from hydrocarbon streams by a more energy efficient and less complicated process.

Other techniques have been put forward to separate hydrocarbon streams into their components.

The use of selective membranes has been suggested. U.S. Pat. Nos. 2,947,687 and 3,043,891 disclose the separation of hydrocarbon mixtures by passing across the face of a non-porous membrane through which at least one component of the hydrocarbon mixture will permeate.

U.S. Pat. No. 3,043,891 teaches a process for increasing the permeation rate of saturated hydrocarbons through non-porous membranes which are capable of separating hydrocarbons according to type, and/or molecular configuration, and/or boiling point or molecular weight. The patent teaches that the permeation process is increased by contacting the membrane during the permeation process with an added hydrocarbon solvent for the membrane. This solvent may contact the membrane on the feed side, the permeate side or on both sides. Representative of such permeation accelerating solvents include aromatics and unsaturated hydrocarbons such as olefins or diolefins. The solvent is described as being a solvent for the membrane, i.e., swells the membrane.

The membranes employed are described as non-porous and include natural or synthetic rubber, gum rubber, chloroprene, neoprene, vinyl polymers such as styrene polymers, polyisobutylene, certain cellulose ethers.

The patent indicates that saturated molecules will permeate through the membrane in the following sequence of increasing selectivity: open chain highly branched hydrocarbons, < open chain with lesser degree of branching; < closed chain (e.g. cycloparaffins) and alkyl cycloparaffins, < straight chain or normal paraffins. Use of the membrane solvent will substantially increase the permeation without substantially altering the selectivity.

U.S. Pat. No. 2,947,687 teaches the separation of hydrocarbons by type through a non-porous membrane using a membrane solvent to enhance the permeation rate. Membrane solvents include substituted hydrocarbons which are soluble in and have solvent power for the membrane. The hydrocarbon solvent is an organic compound containing one or more atoms of halogen, oxygen, sulfur or nitrogen. Thus, materials such as carbontetrachloride, alcohols, ketones, esters, ethers, carboxylic acids, mercaptans, sulfides (e.g. diethylsulfide etc.), nitropropane, nitrobenzene, acetonitrile, formamide, ethylene diamine, etc. may be employed in an amount ranging from 1 to 100% based on total solvent to hydrocarbon feed. The process may be operated at a pressure differential between the feed and permeate zone with the permeate being removed by vacuum. Alternately the permeate can be removed by a sweep stream such as steam, air, butane, etc.

The membrane is non-porous and includes natural or synthetic rubber, vinyl polymers, cellulose esters, cellulose ethers.

The process can use any hydrocarbon source as feed and the separation achieved is in the order: saturated hydrocarbons, < unsaturated hydrocarbons, < aromatics. Saturated hydrocarbons of approximately the same boiling range permeate in the order of increasing selectivity: branched chain, < cyclic-chain, < straight chain configuration, i.e., straight chain paraffins more readily permeate through the membrane.

In an example methyl cyclohexane is separated from an equal volume mixture of methyl cyclohexane and isooctane using 5% methyl ethyl ketone as solvent. An operating pressure differential of 400 mm Hg was maintained and the temperature was 52° C. and 82° C. The methyl cyclohexane preferentially permeated through the membrane.

U.S. Pat. No. 3,956,112 teaches a membrane solvent extraction process. The membrane solvent extraction system is utilized to separate two substantially immiscible liquids and extract a solute through a solvent swollen membrane from one solvent liquid phase to the extracting solvent liquid without direct contact between the liquid phases. The membrane is substantially non-porous. Table III of U.S. Pat. No. 3,956,112 compares the invention of '112 with competing processes One of these processes is described as direct extraction via porous partition. That process is practiced using two immiscible solvents. The driving force is the chemical potential depending on the partition coefficient of the solute in the two solvents. The process employs a porous membrane or partition wall. In that process solutes from one solvent are transferred to the extraction solvent via direct solvent contact.

U.S. Pat. No. 3,140,256 teaches a membrane separation process employing a membrane comprised of a cellulose derivative (e.g. cellulose ester or ether) modified by reaction with aldehydes, organic di isocyanate, organic monoisocyanate, organo-phosphorus chlorides and organo-sulfur chlorides. Hydrocarbon feeds can be separated into these components by type using the membrane, e.g. aromatics can be separated from unsaturated hydrocarbon (olefins or di olefins) and/or from paraffins, or branched chain aliphatic hydrocarbons can be separated from other aliphatic hydrocarbons which have a different number of branched chains. Aromatic hydrocarbons permeate more rapidly than do the saturated (i.e. paraffinic) hydrocarbons. In an example methyl cyclohexane permeated through the membrane more selectively than did iso octane.

U.S. Pat. No. 3,370,102 teaches the membrane separation of aromatics from saturates in a wide variety of feed mixtures including various petroleum fractions, naphthas, oils, and other hydrocarbon mixtures. Expressly recited in '102 is the separation of aromatics from kerosene. The process produces a permeate stream and a retentate stream and employs a sweep liquid to remove the permeate from the face of the membrane to thereby maintain the concentration gradient driving force. U.S. Pat. No. 2,958,656 teaches the separation of hydrocarbons by type i.e. aromatics, unsaturated, saturated by permeating a portion of the mixture through a non-porous cellulose ether membrane and removing permeate from the permeate side of the membrane using a sweep gas or liquid. U.S. Pat. No. 2,930,754 teaches a method for separating hydrocarbons by type, i.e. aromatics and/or olefins from gasoline boiling range mixtures by the selective permeation of the aromatics through certain cellulose ester nonporous membranes. The permeated hydrocarbons are continuously removed from the permeate zone using a sweep gas or liquid. U.S. Pat. No. 4,115,465 teaches the use of polyurethane membranes to selectively separate aromatics from saturates via pervaporation.

U.S. Pat. No. 4,914,064 teaches polyurea/urethane membranes and their use for the separation of aromatics from non-aromatic hydrocarbon. The membrane is characterized by possessing a urea index of at least 20% but less than 100%, an aromatic carbon content of at least 15 mole %, a functional group density of at least about 10 per 1000 grams of polymer and a $C=O/NH$ ratio of less than about 8.

Thin film composites can be prepared either from suspension deposition as taught in U.S. Pat. No. 4,861,628 or from solution deposition as taught in U.S. Pat. No. 4,837,054.

Polyurethane imide membranes and their use for aromatics/non-aromatics separation are the subject of U.S. Pat. No. 4,929,358.

Isocyanurate crosslinked polyurethane membranes and their use for the separation of aromatics from non-aromatics is the subject of U.S. Pat. No. 4,929,357.

U.S. Ser. No. 452,887, filed Dec. 19, 1989 in the names of Black and Schucker, now U.S. Pat. No. 4,962,271 teaches the selective separation of multi-ring aromatic hydrocarbons from distillates by perstraction. The multi-ring aromatics are characterized by having less than 75 mole % aromatic carbon content. Perstractive separation is through any selective membrane, preferably the aforesaid polyurea/urethane, polyurethane imides or polyurethane isocyanurates.

"Microporous Membrane Solvent Extraction" Prasad, R., et al, Separation Science and Technology 22(2&3) 619-640, 1987 examines the phenomenon of dispersion-free solvent extraction through immobilized aqueous-organic interface in a microporous hydrophobic membrane. Expressly investigated was the use of an organic-organic interface to extract aromatics as exemplified by toluene, from a hydrocarbon feedstock, as exemplified by a mixture of toluene in n-heptane, employing a microporous Celgard 2400 polypropylene membrane to partition the feed from the polar extraction solvent, which in this case was NMP. The toluene selectively permeated through the porous Celgard membrane into the NMP thereby reducing the amount of toluene in the feed (raffinate) while increasing the amount of toluene in the permeate phase (extract).

THE PRESENT INVENTION

The present invention is directed to the selective removal of alkyl substituted and alkyl hetero-atom substituted multi-ring aromatic hydrocarbon and alkyl substituted and alkyl heteroatom substituted multi-ring heteroatom containing aromatic hydrocarbons, all of said materials being hereinafter collectively referred to as multi-ring aromatics, and/or toxins, the multi-ring aromatics having a mole % aromatic carbon content of less than 75% from aromatics containing hydrocarbon feed streams by a process comprising contacting the aromatics and/or toxins containing hydrocarbon feed streams with one side of a porous, non-selective partition barrier membrane, simultaneously contacting the other side of said membrane barrier with a selective aromatics extraction solvent and selectively permeating through said barrier the multi-ring aromatics and/or toxins in response to the selective aromatics extraction solvent to produce a permeate enriched in multi-ring aromatics and/or toxins and a retentate lean in multi-ring aromatics and/or toxins but enriched in non-aromatics, paraffinics, and single ring aromatic hydrocarbons.

The alkyl substituted and alkyl/heteroatom substituted multi-ring aromatics and heteroatom containing multi-ring aromatics have less than 75 mole % aromatic carbon. The multi-ring aromatics have at least 2, preferably 3 or more rings, preferably fused rings and one or more alkyl side chains of about 6 to 12 carbon atoms or more in length. The term multi-ring aromatics as used in this specification and the appended claims is meant to include condensed and fused ring aromatics as well as molecules such as biphenyl, diphenyl methane, biphenyl methane, quinoline, carbazol, phenyl thiophene, benzothiophene, dibenz thiophenes etc. and spiro system aromatics consisting of two rings sharing a common atom.

The feed streams which contain hydrocracked multi-ring aromatics and/or toxins which can be separated from single ring aromatics and non-aromatics are virgin hydrocarbon streams and extract oil streams boiling in the 320° to 1100° F. range and having molecular weights ranging from about 125 to 650. They have vicosities in the range of 1.4 to 200 cSt (@ 100° C.).

The prior experimental work (Prassad and Sirhkar) shows that it is possible to separate a simple binary mixture of model compounds comprising one low molecular weight, highly aromatic and one low molecular weight, highly paraffinic molecule. Thus, in the examples the feed consists of only one aromatic, toluene, and one paraffin, n-heptane. These are both low molecular weight molecules having molecular weights of less than or equal to 100 g/mole. The corresponding carbon number $C_7$ is also low as are the boiling points of 110.6° C. (toluene) and 98.4° C. (heptane). The molecular size of these model compounds is relatively small, their molecular diameters being <7 Å.

The aromatic molecule (toluene) which is selectively permeated across the membrane barrier in the prior example is also distinct in being highly aromatic in nature with a mole percent aromatic carbon of over 85%. This selectively permeated aromatic is further distinct in having a single, very short, one carbon, side chain (methyl group) and a single aromatic ring which imparts highly aromatic character to the molecule.

By comparison, in the present invention, the feeds being separated are complex multi-component mixtures containing a wide range of complex, high molecular weight molecules. Within this mixture the individual molecules vary greatly in their degree of aromatic or paraffin character but most are mixed, having both aromatic and paraffinic character. The molecular weights vary because of the complex mixture but in general are high in the range of 125 to 250 g/mole for the jet/diesel stocks and even higher, in the range of 225–650 g/mole, for the lube stocks. The corresponding carbon numbers are also high, typically about $C_9$–$C_{18}$ for diesel stocks and $C_{16}$–$C_{45}$ for lube stocks with total aromaticity in the range of 20 to 95 wt %. The boiling points are high and cover a broad range typically 320°–650° F. for the diesel stocks and 600°–1050° F. for the lube stocks. The molecular diameters would also be larger, in the range of 10–50 Å. Viscosities are also much higher and cover a broad range being about 1.4 to 26.4 sCt (100° C.) for diesel stocks and 5–200 sCt (100° C.) for lube stocks.

The molecules which selectively permeate the membrane barrier in the present invention are aromatic in nature but not as aromatic as those described in the prior art and toxins. The mole percent aromatic carbon is more probably in the lower 40%–75% range compared to the greater than 85% range of toluene. The number of alkyl side chains and their carbon number are each much greater than those of toluene. Typical molecules might contain one or more alkyl side chains of up to 10–12 carbons long in contrast to the single one carbon side chain (methyl group) toluene. The feeds utilized in the present application may also have two or more aromatic rings, some of which may be fused aromatic rings compared to the single aromatic ring of toluene.

An additional characteristic of the present feeds is the presence of S, N, and O heteroatoms in comparison to the non-hetero atom containing-hydrocarbon only structures of toluene and n-heptane. These heteroatoms are distributed throughout the aromatic and alkyl constituents of the individual molecules. Their presence and the polarity they introduce may play an important role in the separation although it is not certain what effect these heteroatoms combined with the varying degrees of aromatic character in these complex molecules, would have on the separation.

Various hydrocarbon streams such as hydro crackate and lube extract oils also contain various toxins which can limit their usefulness. Removal of toxins from hydrocrackate is necessary if hydrocrackate is to be used as a lube base stock. Similarly removal of toxins from lube extract oil is necessary if such oil is to be used for ink and rubber oil production. Lube extract oil is obtained by the selective solvent extraction of a lube oil stream to produce a raffinate phase and an extract phase. The extract phase is rich in aromatic hydrocarbons and contains the bulk of the extraction solvent. Removal of the extraction solvent result in the recovery of the extract oil.

Toxins are removed from hydroarbon oil streams by the membrane extraction process described herein.

The process makes use of a highly porous partition barrier. The barrier can be described as being an ultrafiltration membrane and may be made of ceramic, sintered glass or metal or of a polymeric material such as polyethylene, polypropylene, teflon, cellulose, nylon, etc. and generally has a pore size in the range 100 to 5000 Å. The membrane is, preferably, hydrophobic in nature.

The selective extraction solvents may be any of those normally used in the art including NMP, phenol, furfural, sulfolane, acetonitrile, DMSO, etc. and mixtures thereof. Because the partition barrier prevent commingling of the feed and the solvent, even solvents such as aliphatic poly amines, e.g. as ethylene diamine or diethylenetriamine or triethylene tetramine may be used alone or in combination with the previously recited polar solvents.

Indeed, the use of ethylenediamine as an extraction solvent for light hydrocarbons has been patented (see U.S. Pat. Nos. 3,725,255, 3,725,256 and 3,725,257). However, it cannot be used as a solvent in solvent extraction for lubes because its density (0.899 g/cc) is so close to that of lubes (0.9–1.1 g/cc); settling of the extract from the raffinate solution would be unacceptably slow or even impossible in a conventional extraction tower. However, the use of the porous partition barrier enables one to utilize such a solvent because the settling separation of solvent and oil is avoided.

Test results also show that in the present invention, it is possible to get permeate of 100 LV % aromatics at 25° C. with this solvent with 100 neutral extract feed. For comparison, under similar test conditions, permeate of 70 LV % aromatics was obtained when the more conventional NMP was used.

The higher selectivity obtained with ethylenediamine was unexpected. This is because the pores in the microporous membranes used are much bigger (100–5000 Å) than the molecular size of NMP, ethylenediamine, and lube oils (5–30 Å). Thus the paraffins and the naphthenes would be expected to diffuse to the permeate at the same rate as the aromatics, irrespective of the solvent.

In the present process, the feed and extraction solvent can be contacted at any temperature so long as both the feed and solvent are in the liquid state. Because the separation process is driven by the affinity of the extraction solvent for the aromatic molecules and/or toxins, the process can be run at atmospheric pressure. Indeed, because of the high porosity of the membrane partition barrier the existence of a pressure differential, either by the direct application of pressure on the feed or solvent side or the creation of a vacuum on either side is undesirable as such a pressure differential would physically force feed or solvent across the barrier and thus defeat its purpose.

The multi-ring aromatics and/or toxins rich permeate phase in the extraction solvent may be separated from said solvent by any known technique such as distillation or selective permeation of the solvent through a membrane. The selective separation of extraction solvents from aromatic extracts is the subject of U.S. Pat. No. 4,510,047 which shows such selective solvent permeation through a regenerated cellulose membrane and U.S. Ser. No. 417,333 which teaches the recovery of extraction solvent using interfacially polymerized membranes.

EXAMPLES

EXAMPLE 1

To illustrate the effectiveness of the present process, a run was made on a solvent free 100N extract oil. The microporous membrane used in this run is Celgard 2400, which is a polypropylene membrane with oblong pores approximately $0.02 \times 0.20$ micrometers. The run was made at room temperature ($\sim 25°$ C.)

| Feed | MCT 5 Extract (100N) |
|---|---|
| Temperature, °C | 25 |
| Membrane | Celgard 2400 |
| Sweep | NMP |
| Permeation Rate, Kg/M²/Day | 7 |

| Feed/Product Composition | Feed | Permeate |
|---|---|---|
| Saturates | 44.3 | 29.6 |
| 1 – Ring Aromatic | 18.6 | 21.4 |
| 2 – Ring Aromatic | 16.6 | 21.4 |
| 3 – Ring Aromatic | 20.5 | 27.6 |

In this run, the process is shown to segregate the saturates and 1-ring aromatics from the 2+ ring aromatics in the extract stream. The segregated saturates and 1-ring aromatics can then be blended into the raffinate pool to increase the raffinate yield. Since the permeate from the process is significantly enriched in polynuclear aromatics, the retentate will be significantly enriched in saturates and 1-ring aromatics relative to the extract feed.

Although the example shown is on membrane extraction with NMP, it is expected that other solvent extraction fluids such as phenol and furfural can also be used. It can also be expected that the process would be effective for aromatics/saturates separation in other lube streams such as the distillate.

EXAMPLE 2

To illustrate the effectiveness of ethylenediamine as an extraction solvent, a run was made on a solvent free 100N extract oil. In membrane extraction, because the primary purpose of the membrane is to provide the necessary high surface area for solvent extraction and to prevent gross comingling of the feed and solvent streams, intrinsic selectivity from the membrane is not required. For this study, the run was made with Celgard 2500 which is a micro-porous polypropylene membrane with oblong pores of $0.04 \times 0.20$ micrometers.

| Feed | MCT-5 Extract (100N oil) |
|---|---|
| Temperature, °C | 44 |
| Solvent: | Ethylenediamine |
| Membrane: | Celgard 2500 |
| Flux, kg/m²/day | 2.8 |

| Composition, LV% | Feed | Permeate |
|---|---|---|
| Saturates | 44.3 | 0.0 |
| 1 – Ring Aromatics | 18.6 | 14.7 |
| 2 – Ring Aromatics | 16.6 | 30.1 |
| 3 + Ring Aromatics | 20.5 | 55.2 |

As can be seen from the table above, the run with solvent free 100N extract oil and ethylenediamine was made at 44° C. The flux achieved was 2.8 kg/m²/day. More importantly, the permeate with ethylenediamine is composed of 100% aromatics and no saturates. With the permeate so aromatic, it can be expected that the retentate will be quite paraffinic.

Although data for only one grade of extract oil are shown, it can be expected that ethylenediamine would be equally effective in aromatics/saturates separation for other types and grades of oils. It can also be expected that higher carbon number aliphatic polyamines such as diethylenetriamine or triethylene tetramine would also be effective in aromatics/saturates separation as solvents.

EXAMPLE 3

To illustrate the effectiveness of membrane extraction for toxins removal, a lube extract oil (150N) was obtained and treated. A micro-porous membrane, Celgard 2500, was used to partition the 150N extract oil from the extraction solvent while maintaining intimate contact between the two phases. Celgard 2500 is a micro-porous polypropylene membrane with oblong pores of $0.04 \times 0.20$ micrometers. The extraction solvent used was ethylenediamine. The run was carried out at 90° C. The run length of 24 hours gave a permeate yield of about 20 wt %.

The 150 lube extract oil samples before and after the runs were analyzed by first extracting the samples with DMSO. UV absorbance was then obtained on the DMSO extracted samples. The absorbance at 285 nm provides a measure of the toxicity level of the sample.

As can be seen from the table below, the 150 neutral extract oil showed an absorbance of 14361 units at 285 nm. The retentate from the membrane extraction run showed an absorbance of 12295 units at the same frequency. It can be expected that the retentate would show even lower absorbance (lower toxicity) had the run been carried out to even higher level permeate yield or with a highly selective solvent such as DMSO.

TABLE

| MEMBRANE EXTRACTION FOR TOXIN REMOVAL (1) | | |
|---|---|---|
| Feed | Strathcona 150N Extract | Retentate |
| UV Absorbance, nm | | |
| 280–289 | 14361 | 12295 |
| 290–299 | 11308 | 9631 |

TABLE-continued

MEMBRANE EXTRACTION FOR TOXIN REMOVAL (1)

| Feed | Strathcona 150N Extract | Retentate |
|---|---|---|
| 300-329 | 9241 | 7855 |
| 330-350 | 4144 | 3564 |

(1) Membrane Extraction: 90° C., Ethylenediamine solvent, Celgard 2500 membrane, Flux = 29.0 kg/m²·day, Permeate yield = 20.4 wt %.

In this specification, although only data on 150 neutral grade extract oil are shown, it can be expected that membrane extraction can be used for toxin removal from other hydrocarbon streams such as hydrocrackate.

What is claimed is:

1. A process for separating multi-ring aromatic hydrocarbons having less than 75 mole % aromatic carbon content and/or toxins from hydrocarbon feeds boiling in the 320° to 1100° F. range, said process comprising contacting said hydrocarbon feed with one side of a porous, non-selective membrane, said membrane having a pore size of about 100 to 5000 Å, while simultaneously contacting the other side of said membrane with a selective aromatics extraction solvent, whereby the multi-ring aromatic hydrocarbons and/or toxins in the feed selectively permeate through the porous membrane in response to the extraction solvent.

2. The process of claim 1 wherein the extraction solvent is selected from phenol, furfural, sulfolane, aliphatic polyamines, N-methyl pyrrolidone (NMP) and mixtures thereof.

3. The process of claim 2 wherein the extraction solvent is NMP.

4. The process of claim 2 wherein the extraction solvent is ethylene diamine.

5. The process of claim 1 wherein the multi-ring aromatic and/or toxin permeate in solvent is separated from the solvent by selective permeation of the solvent through a membrane.

* * * * *